(12) United States Patent
Hupperts et al.

(10) Patent No.: US 6,545,154 B2
(45) Date of Patent: Apr. 8, 2003

(54) METHOD FOR THE PRODUCTION OF N-(5-AMINO-2-CYANO-4-FLUORO-PHENYL)-SULPHONAMIDES AND NEW INTERMEDIATE PRODUCTS

(75) Inventors: Achim Hupperts, Düsseldorf (DE); Mark Wilhelm Drewes, Langenfeld (DE); David Erdman, Liberty, MO (US); Reinhard Lantzsch, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 30 days.

(21) Appl. No.: 09/947,263

(22) Filed: Sep. 5, 2001

(65) Prior Publication Data

US 2003/0040626 A1 Feb. 27, 2003

Related U.S. Application Data

(62) Division of application No. 09/463,115, filed as application No. PCT/EP98/04324 on Jul. 24, 1999, now Pat. No. 6,310,206.

(30) Foreign Application Priority Data

Jul. 24, 1997 (DE) ......................... 197 31 783

(51) Int. Cl.⁷ ..................... C07C 255/50; C07C 311/08
(52) U.S. Cl. ..................... 544/298; 544/316; 544/319; 544/408; 546/293; 548/225; 548/228; 548/229; 548/243; 549/65; 549/479; 558/308; 558/413; 558/418
(58) Field of Search .................. 544/298, 316, 544/319, 408; 546/293; 548/225, 228, 229, 243; 549/65, 479; 558/308, 413, 418

(56) References Cited

U.S. PATENT DOCUMENTS

| | | | |
|---|---|---|---|
| 5,464,810 A | 11/1995 | Haas et al. | 504/273 |
| 5,593,945 A | 1/1997 | Andree | 504/243 |
| 5,663,362 A | 9/1997 | Haas et al. | 548/263.2 |
| 5,681,794 A | 10/1997 | Andree et al. | 504/243 |
| 5,756,805 A | 5/1998 | Schallner et al. | 558/412 |
| 5,858,925 A | 1/1999 | Drewes et al. | 504/285 |
| 5,883,102 A * | 3/1999 | Hamley et al. | 514/266.2 |

FOREIGN PATENT DOCUMENTS

JP 7-70041 3/1995

OTHER PUBLICATIONS

Chem. Abstracts, p. 1077, 123:111678e, 3,4–Difluoro–6–nitrobenzonitrile. Yutaka Suzuki and JP 07 70,041.

* cited by examiner

Primary Examiner—Mukund J. Shah
Assistant Examiner—Thomas McKenzie
(74) Attorney, Agent, or Firm—Joseph C. Gil; Richard E. L. Henderson

(57) ABSTRACT

The invention relates to a process for preparing N-(5-amino-2-cyano-4-fluoro-phenyl)-sulphonamides in which, in a first step, 2-amino-4,5-difluoro-benzonitrile is reacted with sulphonyl halides in the presence of an acid acceptor and in the presence of a diluent at temperatures between 0° C. and 150° C. and, in a second step, the N-(2-cyano-4,5-difluoro-phenyl)-sulphonamides and/or N-(2-cyano-4,5-difluoro-phenyl)-sulphonimides obtained in the first step are as pure substances or as mixtures with ammonia in the presence of a diluent reacted at a temperature between 100° C. and 200° C. The invention furthermore relates to novel intermediates of the process.

7 Claims, No Drawings

METHOD FOR THE PRODUCTION OF N-(5-AMINO-2-CYANO-4-FLUORO-PHENYL)-SULPHONAMIDES AND NEW INTERMEDIATE PRODUCTS

This application is a divisional application of Ser. No. 09/463,115, filed Jan. 18, 2000 now U.S. Pat. No. 6,310,206, which is national stage application under 35 USC 371 of International Application PCT/EP98/04324, filed Jul. 24,1999, which claims priority from German application 197 31 783.9, filed Jul. 24, 1997.

TECHNICAL FIELD OF THE INVENTION

The invention relates to a novel process for preparing N-(5-amino-2-cyano-4-fluoro-phenyl)-sulphonamides, which are known as intermediates in the preparation of herbicides, to novel N-(2-cyano-4,5-difluoro-phenyl)-sulphonamides and N-(2-cyano-4,5-difluoro-phenyl)-sulphonimides as intermediates for this process and to processes for their preparation.

BACKGROUND OF THE INVENTION

It is known that certain N-(5-amino-2-cyano-4-fluoro-phenyl)-alkanesulphonamides, such as, for example, N-(5-amino-2-cyano-4-fluoro-phenyl)-methanesulphonamide, are obtained when corresponding halogenated benzene derivatives, such as, for example, 1-amino-4-cyano-2,5-difluoro-benzene, are heated with alkanesulphonamides, such as, for example, methanesulphonamide, in the presence of an acid binder, such as, for example, potassium carbonate, and in the presence of a diluent, such as, for example, N-methyl-pyrrolidone (see EP-A-648772). However, this process affords the desired products in unsatisfactory yields. Accordingly, there is a need for a more favourable preparation process for N-(5-amino-2-cyano-4-fluoro-phenyl)-sulphonamides.

DETAILED DESCRIPTION OF THE INVENTION

It has now been found that N-(5-amino-2-cyano-4-fluoro-phenyl)-sulphonamides of the general formula (I)

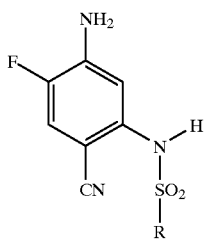

(I)

in which

R represents in each case optionally substituted alkyl, alkenyl, alkinyl, cycloalkyl, cycloalkylalkyl, aryl, arylalkyl, heterocyclyl or heterocyclylalkyl are obtained in high yields and in very good quality when, in a first step, 2-amino-4,5-difluoro-benzonitrile of the formula (II)

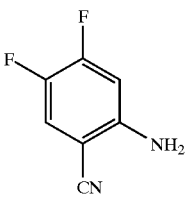

(II)

is reacted with sulphonyl halides of the general formula (III)

$$X—SO_2—R$$ (III)

in which

R is as defined above and

X represents halogen in the presence of an acid acceptor and in the presence of a diluent at temperatures between 0° C. and 150° C. and the resulting N-(2-cyano-4,5-difluoro-phenyl)-sulphonamide intermediates of the general formula (IV) and/or N-(2-cyano-4,5-difluoro-phenyl)-sulphonimide intermediates of the general formula (V)

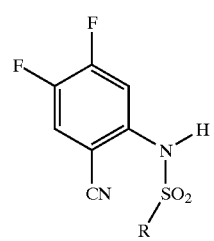

(IV)

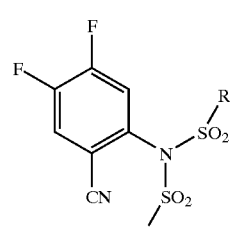

(V)

in which

R is as defined above are reacted as pure substances or as mixtures in a second step with ammonia in the presence of a diluent at temperatures between 100° and 200° C.

Surprisingly, the N-(5-amino-2-cyano-4-fluoro-phenyl)-sulphonamides of the general formula (I) can be obtained by the process according to the invention in a relatively simple manner in high yields and in very good quality, and a pure end product can be prepared via a mixture of intermediates. The intermediates of the formulae (IV) and (V) can be obtained as mixtures in virtually quantitative yield. The main advantage of the process according to the invention is the fact that the use of relatively expensive 2,4,5-trifluoro-benzonitrile can be dispensed with, and the problematic exchange of a fluorine substituent for a sulphonylamino group is not necessary.

The compound 2-amino-4,5-difluoro-benzonitrile of the formula (II) to be used as starting material has not yet been disclosed in the literature; as a novel substance, it also forms part of the subject-matter of the present invention.

The novel compound of the formula (II) is obtained when 4,5-difluoro-2-nitrobenzonitrile of the formula (VI)

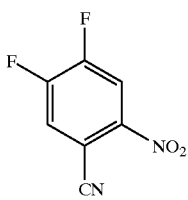

(VI)

is reacted with a reducing agent which is customary for converting aromatic nitro compounds into the corresponding amino compounds, such as, for example, (a) hydrogen in the presence of a catalyst such as, for example, platinum or palladium (where the two last-mentioned compounds are, if appropriate, "poisoned" and supported on a carrier, such as, for example, activated carbon or barium sulphate), in the presence of a diluent, such as, for example, tetrahydrofuran or dioxane, or (b) metals or metal salts, such as, for example, tin, tin(II) chloride, iron (powder) in the presence of an acid, such as, for example, hydrochloric acid or acetic acid, and, if appropriate, additionally in the presence of a diluent, such as, for example, methanol or ethanol, at temperatures between 0° C. and 150° C., preferably between 10° C. and 100° C. (cf. the Preparation Examples).

The intermediates of the formulae (IV) and (V) are not yet known from the literature; as novel substances, they also form part of the subject-matter of the present invention.

The 4,5-difluoro-2-nitro-benzonitrile of the formula (VI) required as precursor is already known (see JP 07070041— cited in Chem. Abstracts 123:111678). According to the patent literature cited, 4,5-difluoro-2-nitro-benzonitrile can be prepared by reaction of 2-bromo-4,5-difluoro-nitrobenzene with copper(I) cyanide in N,N-dimethyl-formamide.

However, the compound of the formula (VI) is also obtained when 3,4-difluorobenzonitrile is reacted with nitric acid, if appropriate in the presence of sulphuric acid, at temperatures between −10° C. and +30° C. (cf. the Preparation Examples).

Surprisingly, this nitration proceeds in a very uniform manner (regioselectively), and hydrolysis of the cyano group, which is to be expected under the nitration conditions, only occurs to a very low extent.

The formula (III) provides a general definition of the sulphonyl halides further to be used as starting materials in the process according to the invention for preparing N-(5-amino-2-cyano-4-fluoro-phenyl)-sulphonamides of the general formula (I).

Preferred meanings in the formulae (I), (III), (IV) and (V) are:

R represents in each case optionally halogen-substituted alkyl, alkenyl or alkinyl having in each case up to 6 carbon atoms, represents in each case optionally halogen- or $C_1$–$C_4$-alkyl-substituted cycloalkyl or cycloalkylalkyl having in each case 3 to 6 carbon atoms in the cycloalkyl group and, if appropriate, 1 to 4 carbon atoms in the alkyl moiety, represents in each case optionally nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy- or $C_1$–$C_4$-alkoxy-carbonyl-substituted aryl or arylalkyl having 6 or 10 carbon atoms in the aryl group and, if appropriate, 1 to 4 carbon atoms in the alkyl moiety, or represents in each case optionally cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted heterocyclyl or heterocyclylalkyl having in each case 3 to 5 carbon atoms and 1 to 2 nitrogen atoms and/or one oxygen or sulphur atom in the heterocyclyl group and, if appropriate, 1 to 4 carbon atoms in the alkyl moiety, and X represents fluorine, chlorine or bromine.

Particularly preferred meanings in the above formulae are:

R represents in each case optionally fluorine- or chlorine-substituted methyl, ethyl, n- or i-propyl, n-, i-, s- or t-butyl, ethenyl, propenyl, butenyl, ethinyl, propinyl or butinyl, represents in each case optionally fluorine-, chlorine-, methyl- or ethyl-substituted cyclopropyl, cyclobutyl, cyclopentyl, cyclohexyl, cyclopropylmethyl, cyclobutylmethyl, cyclopentylniethyl or cyclohexylmethyl, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy-, trifluoromethoxy-, methoxycarbonyl-, ethoxycarbonyl-, n- or i-propoxycarbonyl-substituted phenyl or benzyl, or represents in each case optionally cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted heterocyclyl from the group consisting of furyl, thienyl, oxazolyl, isoxazolyl, pyrazolyl, pyridinyl and pyrimidinyl, and X represents chlorine.

The starting materials of the formula (III) are known chemicals for synthesis.

The first step of the process according to the invention for preparing N-(5-amino-2-cyano-4-fluoro-phenyl)-sulphonamides of the general formula (I) is carried out using an acid acceptor. Suitable acid acceptors are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or -i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylanine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN) or 1,8-diazabicyclo[5.4.0]-undec-7-ene (DBU).

Preferred acid acceptors are basic organic nitrogen compounds.

Suitable diluents for carrying out the first step of the process according to the invention are, especially, inert organic solvents. These include, in particular, aliphatic, alicyclic or aromatic, optionally halogenated hydrocarbons, such as, for example, benzine, benzene, toluene, xylene, chlorobenzene, dichlorobenzen, petroleum ether, hexane, cycloliexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate, sulphoxides, such as dimethyl sulphoxide.

Preferred diluents are aprotic polar organic solvents, in particular acetone or acetonitrile, or else basic organic nitrogen compounds, such as pyridine or 5-ethyl-2-methylpyridine.

When carrying out the first step of the process according to the invention, the reaction temperatures can be varied within a relatively wide range. In general, the first step is carried out at temperatures between 0° C. and 150° C., preferably between 10° C. and 120° C.

The first step of the process according to the invention is generally carried out under atmospheric pressure. However, it is also possible to carry out the process according to the invention under elevated or reduced pressure—generally between 0.1 bar and 10 bar.

For carrying out the first step of the process according to the invention, generally between 1 mol and 10 mol, preferably between 2 mol and 5 mol, of sulphonyl halide of the general formula (III) and between 1 mol and 10 mol, preferably between 2 mol and 5 mol, of acid acceptor are employed per mole of 2-amino-4,5-difluorobenzonitrile of the formula (II).

In a preferred embodiment of the first step of the process according to the invention, the 2-amino-4,5-difluorobenzonitrile of the formula (II) is initially charged together with an acid acceptor and a diluent, and the sulplionyl halide of the general formula (III) is then slowly metered into this mixture with stirring—and, if appropriate, with cooling. The complete reaction mixture is then—if appropriate at elevated temperature—stirred until the reaction has ended.

The mixture of the intermediates of the formulae (IV) and (V)can be worked up in a customary manner. The mixture is, for example, stirred with water or a dilute aqueous acid, the organic phase is separated off, the aqueous phase is, if appropriate, reextracted with an organic solvent which is virtually water-miscible, such as, for example, ethyl acetate, and the combined organic phases are dried and filtered. To isolate the mixture of intermediates, the solvent is carefully distilled off under reduced pressure from the filtrate.

The resulting mixtures of the intermediates of the formulae (IV) and (V)can advantageously be employed without any further purification for the reaction according to the second step of the process according to the invention.

The second step of the process according to the invention is preferably carried out using a diluent. Suitable diluents are, especially, inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, dilsopropyl ether, t-butyl methyl ether, t-pentyl methyl ether, dioxane, tetrahydrofuran or ethylene glycol dimethyl ether or ethylene glycol diethyl ether; ketones, such as, acetone, butanone or methyl isobutyl ketone; nitrites, such as acetonitrile, propionitrile or butyronitrilc; amides, such as N,N-dimethylformamide, N,N-dimethylacetamide, N-methyl-formanilide, N-methyl-pyrrolidone or hexamethylphosphoric triamide; esters, such as methyl acetate or ethyl acetate, sulphoxides, such as dimethyl sulphoxide.

Preference is given to using, as diluents, aprotic polar organic solvents, in particular diisopropyl ether, t-butyl methyl ether, t-pentyl methyl ether, tetrahydrofuran, dioxane, ethylene glycol dimethyl ether or ethylene glycol diethyl ether.

When carrying out the second step of the process according to the invention, the reaction temperatures can be varied within a relatively wide range. In general, the second step is carried out at temperatures between 50° C. and 200° C., preferably between 100° C. and 180° C.

The second step of the process according to the invention is generally carried out in a closed reaction vessel (in particular in an autoclave) under elevated pressure, the pressure depending on the set temperature and the solvent used.

For carrying out the second step of the process according to the invention, generally between 1 and 100 mol, preferably between 5 and 50 mol, of ammonia are employed per mole of the sum of the intermediates of the formulae (IV) and (V).

In a preferred embodiment of the second step of the process according to the invention, the reaction components of the formula (IV) and/or (V) are mixed at room temperature (about 20° C.) with ammonia and a diluent and heated in a closed reaction vessel until the reaction has ended.

Work-up and isolation of the products of the formula (I)can be carried out by customary methods. The reaction mixture is, for example, filtered after cooling, and the solvent is carefully distilled off under reduced pressure from the filtrate. The product can be obtained in this manner as a residue, generally in good quality.

The compounds of the formula (I) preparable by the process according to the invention can be employed as intermediates for preparing herbicidally active compounds (see EP-A-648749, EP-A-648772, WO-A-95/29158).

The intermediates of the formulae (IV) and (V)can also be used as precursors for preparing herbicides (see EP-A 609734).

PREPARATION EXAMPLES

Example 1

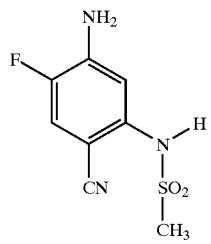

Step 1

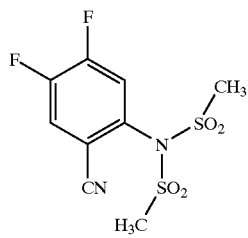

15 g (130 mmol) of methanesulphonyl chloride are added dropwise with stirring to a mixture of 3.7 g (24 mmol) of 2-amino-4,5-difluoro-benzonitrile, 5.0 g (33 mmol) of 1,8-diazabicyclo[5.4.0]-undec-7-ene (DBU) and 50 ml of pyridine, and the reaction mixture is then heated at 50° C. for approximately one hour. The mixture is subsequently concentrated under water pump vacuum, the residue is stirred with 100 ml of 20% strength hydrochloric acid and 10 ml of ethyl acetate and the crystalline product is isolated by filtration with suction.

This gives 3.3 g (44% of theory) of 4,5-difluoro-2-(bis-methanesulphonyl-amino)-benzonitrile of melting point 144° C.

Step 2

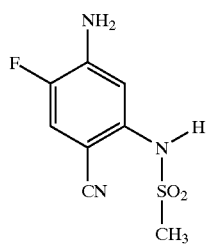

In a 100 ml autoclave, 2 ml of ammonia are condensed and 2.0 g (6.4 mmol) of 4,5-difluoro-2-(bis-methanesulphonyl-amino)-benzonitrile and 40 ml of tetrahydrofuran are added. The reaction mixture is then heated in the closed autoclave at 150° C. for 15 hours. After cooling, the mixture is filtered and the filtrate is concentrated under water pump vacuum. Washing with 2N hydrochloric acid and with water gives 0.50 g (34% of theory) of N-(5-amino-2-cyano-4-fluoro-phenyl)-methanesulphonamide of melting point 235° C.

Example 2

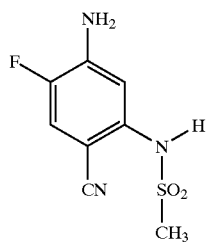

Step 1

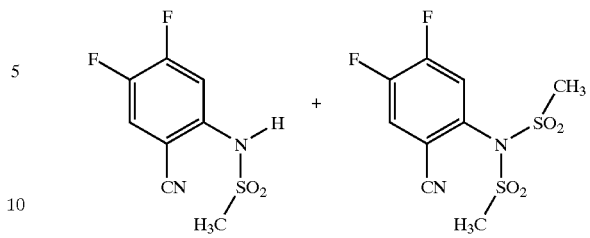

4.6 g (40 mmol) of methanesulphonyl chloride are added dropwise with stirring to a mixture of 1.54 g (10 mmol) of 2-amino-4,5-difluoro-benzonitrile, 4.0 g (40 mmol) of triethylamine and 50 ml of acetonitrile, and the complete reaction mixture is then heated under reflux for approximately one hour. After cooling, the mixture is stirred with 100 ml of ice-water for 30 minutes, the phases are separated and the aqueous phase is reextracted with 50 ml of ethyl acetate. The combined organic phases are washed with saturated aqueous ammonium bicarbonate solution and then with water, dried using sodium sulphate and filtered. The solvent is carefully distilled off from the filtrate under water pump vacuum.

This gives 2.9 g of a mixture of 43% of 4,5-difluoro-2-(bis-methyl-sulphonylamino)-benzonitrile and 57% of 4,5-difluoro-2-methylsulphonylamino-benzonitrile (according to GC/MS) as residue, corresponding to a quantitative overall yield.

Step 2

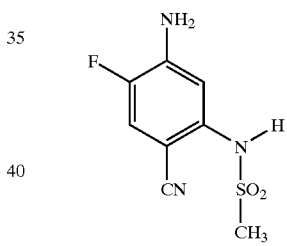

In a 100 ml autoclave, 4.5 ml of ammonia are condensed and the product mixture obtained according to step 2 (2.9 g) and 50 ml of tetrahydrofuran are added. The reaction mixture is then heated in the closed autoclave at 150° C. for 15 hours. After cooling, the mixture is filtered and the filtrate is concentrated under water pump vacuum. Washing with 2N hydrochloric acid and with water gives 1.0 g (44% of theory) of N-(5-amino-2-cyano-4-fuoro-phenyl)-methanesulphonamide of melting point 235° C.

Example 3

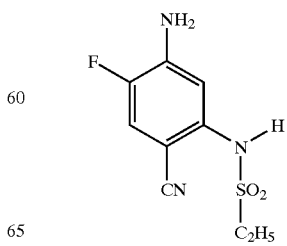

Step 1

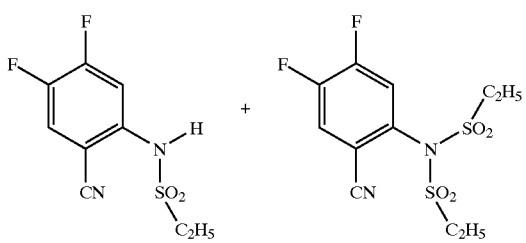

5.1 g (40 mmol) of ethanesulphonyl chloride are added dropwise with stirring to a mixture of 1.54 g (10 mmol) of 2-amino-4,5-difluoro-benzonitrile, 4.0 g (40 mmol) of triethylamine and 50 ml of acetonitrile, and the complete reaction mixture is then heated under reflux for approximately two hours. After cooling, the mixture is stirred with 100 ml of ice-water for 30 minutes, the phases are separated and the aqueous phase is reextracted with 50 ml of ethyl acetate. The combined organic phases are dried using sodium sulphate and filtered. The solvent is carefully distilled off from the filtrate under water pump vacuum.

This gives 3.0 g of a mixture of 67% of 4,5-difluoro-2-(bis-ethyl-sulphonylamino)-benzonitrile and 33% of 4,5-difluoro-2-ethylsulphonylamino-benzonitrile (according to GC/MS) as residue, corresponding to a quantitative overall yield.

Step 2

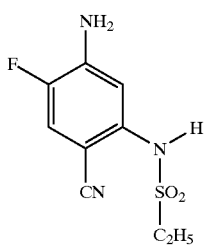

In a 100 ml autoclave, 4 ml of ammonia are condensed and 3.0 g of the product mixture from Step 1 and 50 ml of tetrahydrofuran are added. The reaction mixture is heated in the closed autoclave at 150° C. for 15 hours and, after cooling, filtered. The filtrate is concentrated under water pump vacuum, washed with 2N hydrochloric acid and with water and dried.

This gives 1.1 g (45% of theory of a 95.5% pure product) of 4-amino-5-fluoro-2-ethylsulphonylamino-benzonitrile of melting point 170° C.

STARTING MATERIAL OF THE FORMULA (II)

Example (II-1)

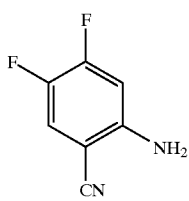

3.68 g (20 mmol) of 4,5-difluoro-2-nitro-benzonitrile are dissolved in 40 ml of dioxane, and 300 mg of platinum on carbon (5%) are added. The suspension is subsequently stirred under hydrogen at from 20° C. to 25° C. until 1.45 litres of hydrogen have been taken up. The mixture is then filtered through silica gel and the filtrate is concentrated under water pump vacuum. The residue is then worked up by column chromatography (silica gel, hexane/ethyl acetate).

This gives 2.19 g (72% of theory) of 2-amino-4,5-difluoro-benzonitrile of melting point 114° C. and, from another fraction 0.52 g (15% of theory) of 2-amino-4,5-difluoro-benzamide.

Example (II-2)

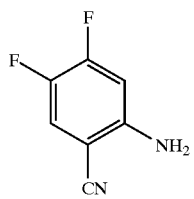

11.0 g (59 mmol) of 4,5-difluoro-2-nitro-benzonitrile are dissolved in 175 ml of acetic acid ("glacial acetic acid"), and 20 g (358 mmol) of iron (powder) are added a little at a time. During the addition, the reaction temperature is kept at from 40° C. to 50° C. by cooling using a water bath. The complete reaction mixture is then stirred at 50° C. for another 3 hours. After cooling to room temperature, the mixture is poured into 200 ml of ice-water. The mixture is extracted twice with 50 ml of ethyl acetate each time, and the organic extract solutions are combined, washed with saturated sodium bicarbonate solution and then with water, dried with sodium sulphate and filtered. The filtrate is concentrated under water pump vacuum and the residue is worked up by column chromatography (silica gel, hexane/ethyl acetate).

This gives 7.7 g (85% of theory) of 2-amino-4,5-difluoro-benzonitrile of melting point 114° C.

STARTING MATERIAL OF THE FORMULA (VI)

Example (VI-1)

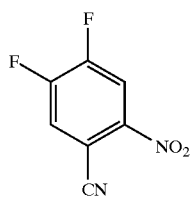

A mixture of 40 ml of sulphuric acid (97% strength) and 30 ml of nitric acid (98% strength) is cooled to 0° C. 13.9 g (0.10 mol) of 3,4-difluoro-benzonitrile are then added a little at a time such that the reaction temperature stays below 5° C. The complete reaction mixture is stirred at from 5° C. to 10° C. for 5 hours and, after warming to 20° C., stirred for another 2 hours. The mixture is subsequently poured onto 400 g of ice, and the crystalline product is isolated by filtration with suction and taken up in 20 ml of methylene chloride. The aqueous phase is reextracted twice using 30 ml of methylene chloride each time. The organic phases are combined, washed with saturated sodium bicarbonate solution and with water, dried with sodium sulphate and filtered. The solvent is carefully distilled off from the filtrate under water pump vacuum.

This gives 10.2 g (55% of theory) of 4,5-difluoro-2-nitro-benzonitrile of melting point 75° C.

What is claimed is:

1. A 2-amino-4,5-difluoro-benzonitrile of the formula (II)

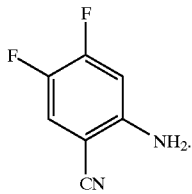

(II)

2. A process for preparing a 2-amino-4,5-difluoro-benzonitrile, comprising the step of reacting a 4,5-difluoro-2-nitro-benzonitrile with a reactant to convert an aromatic nitro compound into a corresponding amino compound, at a temperature of between 0° C. and 150° C.

3. A process for preparing a N-(5-amino-2-cyano-4-fluoro-phenyl)-suphonamide of the formula (I)

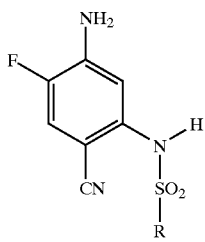

(I)

wherein

R represents in each case unsubstituted or substituted alkyl, alkenyl, alkynyl, cycloalkyl, cycloalkylalkyl, aryl, arylalkyl, heterocyclyl or heterocyclylalkyl, comprising the steps of:

a) reacting a 2-amino-4,5-difluoro-benzonitrile of the formula (II)

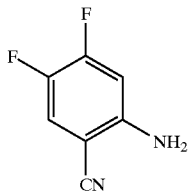

(II)

with a sulphonyl halide of the formula (III)

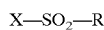

X—SO$_2$—R     (III)

wherein

R is as defined above and

X represents halogen in the presence of an acid acceptor and in the presence of a diluent at a temperature between 0° C. and 150° C. and b) reacting the N-(2-cyano-4,5-difluoro-phenyl)-sulphonimide of the formula (V) obtained in step a)

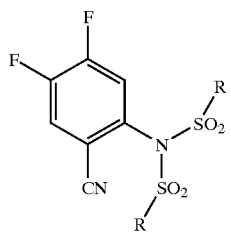

(V)

wherein

R is as defined above with ammonia in the presence of a diluent at a temperature between 100° C. and 200° C.

4. The process of claim 3, wherein

R represents in each case unsubstituted or halogen-substituted alkyl, alkenyl or alkynyl having in each case up to 6 carbon atoms, represents in each case unsubstituted or halogen- or $C_1$–$C_4$-alkyl-substituted cycloalkyl or cycloalkylalkyl having in each case 3 to 6 carbon atoms in the cyclo-alkyl group and 1 to 4 carbon atoms in the alkyl moiety, represents in each case unsubstituted or nitro-, cyano-, halogen-, $C_1$–$C_4$-alkyl-, $C_1$–$C_4$halogenoalkyl-, $C_1$–$C_4$-alkoxy-, $C_1$–$C_4$-halogenoalkoxy- or $C_1$–$C_4$alkoxy-carbonyl-substituted aryl or arylalkyl having 6 or 10 carbon atoms in the aryl group and 1 to 4 carbon atoms in the alkyl moiety, or represents in each case unsubstituted or cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted heterocyclyl or hetero-cyclylalkyl having in each case 3 to 5 carbon atoms and 0, 1 or 2 nitrogen atoms and zero or one oxygen or sulphur atom in the heterocyclyl group and 1 to 4 carbon atoms in the alkyl moiety, and X represents fluorine, chlorine or bromine.

5. The process of claim 3, wherein

R represents in each case unsubstituted or fluorine- or chlorinesubstituted methyl, ethyl, n- or i-propyl, n-, i-, s- or t-butyl, ethenyl, propenyl, butenyl, ethinyl, propinyl or butinyl, represents in each case unsubstituted or fluorine-, chlorine-, methyl- or ethyl-substituted cyclopropyl, cyclobutyl, cyclopentyl, cyclohexyl, cyclopropyl methyl, cyclobutyl methyl, cyclopentylmethyl or cyclohexylmethyl, represents in each case unsubstituted or nitro-, cyano-, fluorine-, chlorine-, bromine-, methyl-, ethyl-, n- or i-propyl-, n-, i-, s- or t-butyl-, trifluoro-methyl, methoxy-, ethoxy-, n- or i-propoxy-, n-, i-, s- or t-butoxy-, difluoromethoxy-, trifluoromethoxy-, methoxycarbonyl-, ethoxycarbonyl-, n- or i-propoxycarbonyl-substituted phenyl or benzyl, or represents in each case unsubstituted or cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted hetero-cyclyl from the group consisting of furyl, thienyl, oxazolyl, isoxazolyl, pyrazolyl, pyridinyl and pyrimidinyl, and X represents chlorine.

6. The process of claim 3 wherein the acid acceptor is a basic organic nitrogen compound.

7. The process of claim 3 wherein the diluent in step a) is selected from the group consisting of acetone and acetonitrile and the diluent in step b) is selected from the group consisting of pyridine and 5-ethyl-2-methyl-pyridine.

* * * * *